United States Patent [19]

Hoffmann

[11] 4,200,766
[45] Apr. 29, 1980

[54] PREPARATION OF HYDROXYCITRONELLOL

[75] Inventor: Werner Hoffmann, Neuhofen, Fed. Rep. of Germany

[73] Assignee: BASF Aktiengesellschaft, Fed. Rep. of Germany

[21] Appl. No.: 961,705

[22] Filed: Nov. 17, 1978

[30] Foreign Application Priority Data

Dec. 15, 1977 [DE] Fed. Rep. of Germany ....... 2755945

[51] Int. Cl.$^2$ .............................................. C07C 29/04
[52] U.S. Cl. .................................... 568/875; 568/860
[58] Field of Search ................................ 568/875, 860

[56] References Cited

FOREIGN PATENT DOCUMENTS

| | | | |
|---|---|---|---|
| 675355 | 12/1963 | Canada ..................................... | 568/875 |
| 886763 | 1/1962 | United Kingdom ..................... | 568/875 |
| 1167776 | 10/1969 | United Kingdom ..................... | 568/875 |

OTHER PUBLICATIONS

Matsubara et al., "Yuki Gosei Kagaku Kyokai," Shi 31, (1973) 11, 924–927.
Matsubara et al., "C.A.," 81:37653p (1974).
Ansari et al., "C.A.," 78:97112j (1973).
Nomori et al., "C.A.," 77:100828j (1972).
Ansari et al., II, "C.A.," 83:136733n (1975).
Naves et al., "Helv. Chim Acta," vol. 44, Fasc(7) (1961), No. 228–229, p. 1867.
Naves et al., "Bull. Soc. Chim France," vol. 23, p. 1768 (1956).
Desalbres et al., "Bull. Soc. Chim France," vol. 23, p. 761 (1956).

*Primary Examiner*—Norman Morgenstern
*Attorney, Agent, or Firm*—Keil & Witherspoon

[57] ABSTRACT

An improved process for the preparation of hydroxycitronellol by an addition reaction of water with citronellol. This reaction takes place directly on heating a homogeneous solution of citronellol in a mixture of water and an α-methyl-branched lower alkanol in the presence of a strongly acid ion exchanger.

Hydroxycitronellol may be used as a fragrance material and is an important intermediate for the preparation of the highly desired scent hydroxycitronellal.

2 Claims, No Drawings

PREPARATION OF HYDROXYCITRONELLOL

The present invention relates to an improved process for the preparation of hydroxycitronellol (I; 3,7-dimethyl-octane-1,7-diol) by an addition reaction of water with citronellol (II; 3,7-dimethyl-oct-6-en-1-ol)

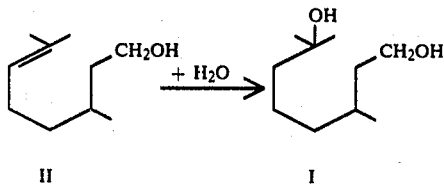

in the presence of a cation exchanger.

"Yuki Gosei Kagaku Kyokai" Shi 31 (1973) 11, 924–27 discloses that hydroxycitronellol I, required as a fragrance material and in particular as an intermediate for the preparation of the highly desired fragrance material hydroxycitronellal, may be prepared by carrying out an addition reaction between citronellol and a lower carboxylic acid, eg. acetic acid, in the presence of a cation exchanger, and then hydrolyzing the reaction product. This process has the disadvantage that, firstly, only low conversions are achieved, and, secondly, it is not hydroxycitronellol itself but its carboxylic acid ester which is formed; this ester must be hydrolyzed after isolation, a procedure which in industrial operation is highly uneconomical.

It is an object of the present invention to provide a method of preparing hydroxycitronellol which is very simple and therefore cheap and avoids the above disadvantages.

We have found, surprisingly, that this object is achieved and that hydroxycitronellol (I) is obtained in an economical and technically simple manner by addition reaction of water with citronellol (II) if a homogeneous solution, containing, per kilogram of II, from 0.1 to 10 liters, preferably from 1 to 5 liters, of water as well as an α-methyl-branched primary, secondary or tertiary $C_3$–$C_5$-alkanol is treated with a strongly acid cation exchanger at from 40° to 120° C. and thereafter the reaction mixture is worked up in the conventional manner by distillation to give the desired product.

Accordingly, using the process of the invention it is possible, surprisingly, to dispense with the presence of the relatively expensive lower carboxylic acids and with the subsequent, expensive, hydrolysis of the carboxylic acid ester formed.

The starting compound II is commercially available as natural or synthetic citronellol.

Suitable alkanols which accord with the above definition are, in particular, propan-2-ol, 2-methyl-propanol (isobutanol), 2-methyl-propan-2-ol (tert.-butanol) and butan-2-ol.

The amount of these alkanols is advantageously chosen so that the mixture of II and water will just form a homogeneous solution therein at room temperature. Depending on the nature of the alkanol and on the amount of water used, from about 5 to 20 liters of alkanol per kilogram of II are required for this purpose. Larger amounts of alkanol, for example up to twice the amount, are not detrimental but in general also offer no advantage.

The amount of water has a broad effect on the rate of reaction, in accordance with the known rules. Within the range stated above, particularly good results are achieved by using from 1 to 5 liters of water per kilogram of II. Larger amounts than 10 liters of water per kilogram of II are economically undesirable, since they result in an excessively larger volume of liquid.

For the purposes of the present invention, strongly acid cation exchangers are synthetic resin ion exchangers, ie. high-polymer three-dimensional networks of carbon chains (matrix) in the form of a gel structure carrying —$SO_3^\ominus$ groups or —$SO_3^\ominus$ and —$O^\ominus$ groups as the charged groups (fixed ions). Essentially, the products concerned are commercial cation exchangers based on polystyrene-sulfonic acid resins or phenolsulfonic acid resins and available, for example, under the following tradenames: Lewatit S 100, Lewatit S 115, Lewatit SP 1080, Lewatit SC 102, Lewatit SPC 118, Amberlite IR 120, Amberlite IR 200, Amberlyst 15, Dowex 50, Permutit RS, Wofatit KPS 200, Duolite C-3, Duolite C-10, Duolite C-25, Wofatit F, Wofatit D, Wofatit P, Zeoxex (Zeocarb H), Nalcite HCR, Nalcite HGR, Nalcite HDR, Permutit Q and Permutit RS.

Particularly advantageous results in respect of conversion and reaction time are achieved with cation exchangers having an exceptionally large number of active centers per unit of surface area. Such exchangers include, for example, the particularly finely divided cation exchangers, eg. Lewatit SPC 108, Lewatit SP 1080 and Lewatit SPC 118 and the coarse-pored ion exchangers, eg. Amberlyst 15.

The cation exchanger is employed in the commercial hydrated form, but is washed, before use in the reaction, with from about 5 to 10 times its volume of the relevant alcohol-water mixture.

Further details of the preparation, properties and use of the acid cation exchangers may be found in Ullmanns Encyclopädie der technischen Chemie, 3rd edition, volume 8, 1957, pages 787 et seq., especially pages 806–811 and 814–822.

For batchwise operation, the resins are advantageously used in an amount of from 1 to 5 liters per kilogram of II. If the reaction is carried out continuously by passing the aqueous alcoholic solution of II through an exchanger column, it is advantageous to choose conditions corresponding to 1 kg of II being passed, per hour, over 5–10 liters of the resin. It is advantageous to wash the exchanger resin, before using it for the first time, with an aqueous solution of the alkanol, having a composition which roughly corresponds to the water/alkanol ratio in the solutions of II.

The preferred reaction temperatures are from 50° to 90° C. Since the reaction concerned is an equilibrium reaction, complete conversion is not achieved; instead, the maximum conversion is from 40 to 70% depending on the temperature and on the amount of water. The optimum conversions, from the point of view of the economics, are from about 50 to 65% of the equilibrium concentration, because at higher conversions the reaction slows down disproportionately to the increase in conversion. The stated conversions require reaction times of from about 1 to 20 hours depending on the amount of the cation exchanger. The conversion can be followed by gas chromatography.

When the desired conversion has been reached, the solution is separated from the cation exchanger and is worked up by distillation in the conventional manner. The unconverted starting compound, the alkanol and the water are advantageously recycled to the reaction stage. The cation exchanger retains its activity unchanged over long periods of operation and therefore only requires occasional conventional regeneration.

Hydroxycitronellol, obtained by the process of the invention, may be used as a fragrance material and is an important intermediate for the preparation of the highly desired product hydroxycitronellal.

Using the process according to the invention, hydroxycitronellal can be obtained by a technically simple and cheap method.

EXAMPLE 1

A solution of 50 g of citronellol, 200 ml of water and 300 ml of isopropanol was stirred for 17 hours at 80° C. with 100 ml of the strongly acid cation exchanger Lewatit S 100 (particle size: 0.3–1 mm), which had been washed beforehand with a 5-fold volume of a mixture of isopropanol and water in the ratio of 3:2. After 17 hours, about 61% of citronellol had been converted and the equilibrium had been reached.

Working up the solution conventionally by distillation after removing the exchanger resin gave 19 g of unconverted citronellol and 32 g of hydroxycitronellol, corresponding to a yield of 94% based on citronellol converted. Boiling point = 99°–101° C./0.03 mbar; $n_D^{25} = 1.4579$.

EXAMPLES 2 to 8

A solution of 50 g of citronellol, 200 ml of water and 300 ml of isopropanol was stirred at 80° C., for the reaction time shown in the Table, with the cation exchanger which is also shown in the Table and had been pretreated as described in Example 1; the reaction mixture was then separated from the exchanger resin and worked up by distillation. The results obtained are shown in the Table below:

| Cation exchanger | Reaction time [h] | Conversion | Yield based on II converted |
|---|---|---|---|
| Lewatit SP 120 | 12 | 62% | 92–94% |
| Lewatit SPC 108 | 5 | 64% | " |
| Amberlyst 15 | 8 | 61% | " |
| Amberlite 200 | 9 | 61% | " |
| Lewatit SP 1080 | 6 | 61% | " |
| Lewatit SC 102 | 15 | 61% | " |
| Lewatit SPC 118 | 7 | 64% | " |

EXAMPLE 9

A solution of 50 g of citronellol in 50 ml of water and 300 ml of isobutanol was stirred for 10 hours at 80° C. with 100 ml of the strongly acid cation exchanger Lewatit SC 102 which had beforehand been washed with a 5-fold volume of a mixture of isobutanol and water in the ratio of 6:1. About 45% of citronellol were converted and equilibrium was reached.

About 4% of 3,7-dimethyl-7-iso-butoxy-octan-1-ol were detected as a by-product. The reaction mixture was separated from the ion exchanger and hydroxycitronellol was isolated from the mixture by distillation, in 84% yield based on citronellol converted.

EXAMPLE 10

A solution of 50 g of citronellol, 200 ml of water and 600 ml of butan-2-ol was stirred for 12 hours at 80° C. with 100 ml of the strongly acid cation exchanger Lewatit SPC 108, which had beforehand been washed with a 5-fold volume of a mixture of butan-2-ol and water in the ratio of 3:2. About 47% of citronellol were converted and equilibrium was reached.

The reaction mixture was separated from the ion exchanger and on distillation gave 32 g of hydroxycitronellol, corresponding to a yield of 94%, based on citronellol converted.

I claim:

1. A process for the preparation of hydroxycitronellol (I) by hydration of citronellol (II) with water which comprises contacting a homogeneous solution, containing, per kilogram of II, from 0.1 to 10 liters of a mixture of water and an α-methyl-branched $C_3$–$C_5$-alkanol with a strongly acidic cation exchange resin at a temperature of from 40° to 120° C. and thereafter recovering I by conventional distillation.

2. The process of claim 1, wherein from 1 to 5 liters of water are contained in the solution per kilogram of II.

* * * * *